US012751962B2

(12) United States Patent
Garcia-Rodenas et al.

(10) Patent No.: US 12,751,962 B2
(45) Date of Patent: Oct. 6, 2026

(54) COMPOSITIONS COMPRISING HUMAN MILK OLIGOSACCHARIDES FOR USE IN A SUBJECT TO SUPPORT MATURATION OF SLEEPING PATTERNS

(71) Applicant: SOCIETE DES PRODUITS NESTLE S.A., Vevey (CH)

(72) Inventors: Clara Lucia Garcia-Rodenas, Forel (CH); Jonas Hauser, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 578 days.

(21) Appl. No.: 18/255,774

(22) PCT Filed: Dec. 3, 2021

(86) PCT No.: PCT/EP2021/084198
§ 371 (c)(1),
(2) Date: Jun. 2, 2023

(87) PCT Pub. No.: WO2022/117830
PCT Pub. Date: Jun. 9, 2022

(65) Prior Publication Data

US 2024/0000818 A1 Jan. 4, 2024

(30) Foreign Application Priority Data

Dec. 4, 2020 (EP) .................................... 20211830

(51) Int. Cl.

| | |
|---|---|
| ***A61K 31/702*** | (2006.01) |
| ***A23L 33/00*** | (2016.01) |
| ***A23L 33/21*** | (2016.01) |
| ***A61P 25/00*** | (2006.01) |

(52) U.S. Cl.
CPC ............ *A61K 31/702* (2013.01); *A23L 33/21* (2016.08); *A23L 33/40* (2016.08); *A61P 25/00* (2018.01)

(58) Field of Classification Search
None
See application file for complete search history.

(56) References Cited

U.S. PATENT DOCUMENTS

| | | | | |
|---|---|---|---|---|
| 2011/0206649 | A1 * | 8/2011 | Bergonzelli Degonda .................. | A61K 35/747 424/93.4 |
| 2015/0305384 | A1 | 10/2015 | Chichlowski et al. | |
| 2018/0333426 | A1 | 11/2018 | Chichlowski et al. | |
| 2019/0029303 | A1 | 1/2019 | Binia et al. | |
| 2019/0083003 | A1 * | 3/2019 | Lee ...................... | A61B 5/4812 |
| 2021/0139842 | A1 * | 5/2021 | Odamaki ................ | A61P 37/00 |

FOREIGN PATENT DOCUMENTS

| | | | | |
|---|---|---|---|---|
| EP | 3407897 A1 | | 12/2018 | |
| WO | 2016139328 | | 9/2016 | |
| WO | 2017190755 | | 11/2017 | |
| WO | WO-2019087140 A1 | * | 5/2019 | ........... A61K 31/702 |
| WO | 2020120426 A1 | | 6/2020 | |

OTHER PUBLICATIONS

Wu, K. J., Chen, Y. H., Bae, E. K., Song, Y., Min, W., & Yu, S. J. (2020). Human milk oligosaccharide 2'-fucosyllactose reduces neurodegeneration in stroke brain. Translational Stroke Research, 11(5), 1001-1011. (Year: 2020).*
Wicinski et al. "Human Milk Oligosaccharides: Health Benefits, Potential Applications in Infant Formulas, and Pharmacology" Nutrients, 2020, vol. 12, 14 pages.
Reverri et al. "Review of the Clinical Experiences of Feeding Infants Formula Containing the Human Milk Oligosaccharide 2'-Fucosyllactose" Nutrients, 2018, vol. 10, 11 pages.
Chinese Office Action for Appl No. 202180080351.6 dated Jun. 3, 2025, 7 pages.
European Office Action for Appl No. 21 819 896.8-1105 dated Aug. 6, 2025, 5 pages.

* cited by examiner

*Primary Examiner* — Dale R Miller
(74) *Attorney, Agent, or Firm* — K&L Gates LLP

(57) ABSTRACT

The present invention relates to a nutritional composition comprising fucosylated human milk oligosaccharides for improving sleep maturation in a subject.

12 Claims, 1 Drawing Sheet

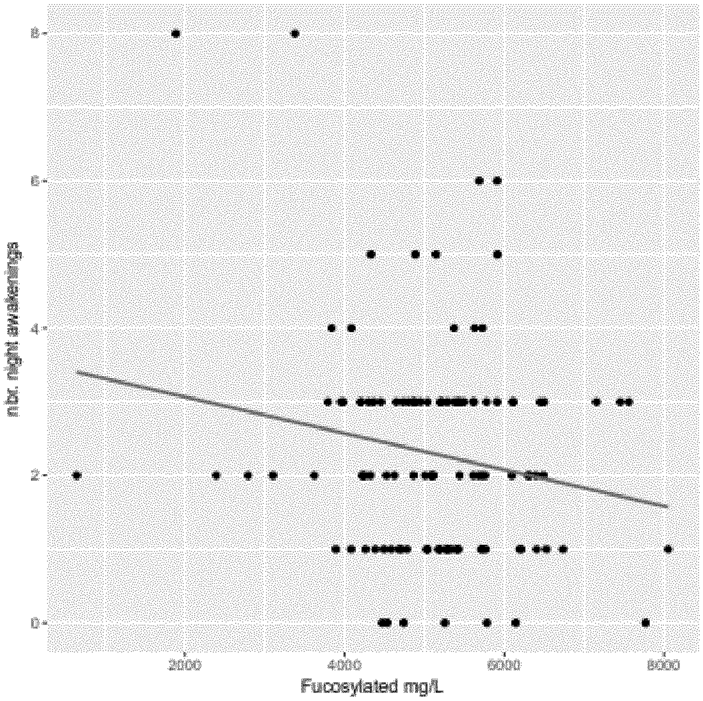
nbr. night awakenings
0
2
4
6
8
2000
4000
6000
8000
Fucosylated mg/L

COMPOSITIONS COMPRISING HUMAN MILK OLIGOSACCHARIDES FOR USE IN A SUBJECT TO SUPPORT MATURATION OF SLEEPING PATTERNS

CROSS REFERENCE TO RELATED APPLICATIONS

The present application is a National Stage of International Application No. PCT/EP2021/084198, filed on Dec. 3, 2021, which claims priority to European Patent Application No. 20211830.3, filed on Dec. 4, 2020, the entire contents of which are being incorporated herein by reference.

FIELD OF THE INVENTION

This invention relates to nutritional compositions comprising human milk oligosaccharides for use in a subject to support maturation of sleeping patterns. In particular, the nutritional composition comprises fucosylated oligosaccharides.

BACKGROUND OF THE INVENTION

Breast feeding is considered as the ideal source of nutrition and is the preferred choice for feeding infants up to at least 6 months of age. Consequently, human milk (HM) has long been considered as the model for the design of infant formulas (IF). Even many improvements in the nutrient composition of IF have been made during the last decades, there are still important differences in composition as well as in functional benefits conveyed by HM.

Identifying the potential relationship between Human milk oligosaccharides (HMOs) and early brain development has gained substantial interests in recent years. Preliminary evidence based on animal studies have implicated that human milk oligosaccharides (HMOs) could play a significant role in the development of the central nervous system and therefore in the associated functions.

Reduced sleep has been associated with multiple negative effects, such as decreased cognitive development, mood regulation, and overall health (L. J. Meltzer, J. A. Mindell Sleep and sleep disorders in children and adolescents Psychiatr Clin North Am, 29 (2006), pp. 1059-1076). Specifically, short sleep duration and poor sleep quality has been associated with obesity (E. M. Taveras, S. L. Rifas-Shiman, E. Oken, et al. Short sleep duration in infancy and risk of childhood overweight Arch Pediatr Adolesc Med, 162 (2008), pp. 305-311) and behavioral problems (B. Zuckerman, J. Stevenson, V. S. Bailey Sleep problems in early childhood: continuities, predictive factors, and behavioral correlates Pediatrics, 80 (1987), pp. 664-671). The most common sleep disturbances in infants and children are those related to wakefulness (i.e. either difficulties in settling at bedtime or failure to sleep through the night without interruptions). It has been estimated that these disturbances affect 15 to 35% of infants aged less than 24 months (France et al, "Infant Sleep Disturbance: Description of a problem behaviour process", Sleep Medicine Reviews, Vol 3, No 4, pp 265-280, 1999). Furthermore, these sleep disturbances might look different at different age as sleep pattern mature in early life, switching from a more fragmented non-circadian sleep to long unbroken sleep session following a circadian rhythm (Anders T F, Keener M, Bowe T R, Shoaff B A. A longitudinal study of nighttime sleep-wake patterns in infants from birth to one year. In: Call J D, Galenson E, Tyson R L (eds):Frontiers of Infant Psychiatry. New York: Basic Books, 1983:50-166).

Ji et al (Public Health Nutrition, 2017 March; 20(4):687-701), reviewed the existing literature relating to the relationship between micronutrients status and sleep patterns and concluded evidence has emerged that suggests a link between dietary/circulating micronutrients and sleep.

The potential impact of HMOs on gut microbiota have been implicated since HMOs are largely metabolized in the intestinal tracts. In contrast, the potential effects of HMOs on brain functional development are less studied, and most studies in this field focused on learning and memory. For example, using chronic oral administration of 2'FL rodents, Vazquez et al (2015) Journal of nutritional biochemistry 26(5):455-465 demonstrated that the treated animals exhibit significantly better learning and working memory functions. Nevertheless, to the best of our knowledge, the present study is the first study reporting human results and investigating impact of HMO on maturation of sleep patterns.

There is a need to deliver such health benefits in the subject in a manner that does not induce side effects and/or in a manner that is easy to deliver, and well accepted by the parents or health care practitioners. There is also a need to deliver such benefits in a manner that does keep the cost of such delivery reasonable and affordable by most.

SUMMARY OF THE INVENTION

In one aspect, the present invention relates to a nutritional composition comprising fucosylated human milk oligosaccharides for improving sleep maturation in a subject.

The composition for use above, wherein the oligosaccharide(s) is/are present in a total amount of from 50 mg to 5000 mg/L for example from 50 mg to 2500 mg/L for example from 60 mg to 2000 mg per L, from 80 mg to 1000 mg per L of the nutritional composition.

In another aspect, the present invention relates to a nutritional composition being an infant formula, a starter infant formula, a follow-on or follow-up infant formula, a baby food, an infant cereal composition, a fortifier or a supplement.

BRIEF DESCRIPTION OF FIGURES

FIG. 1 Correlation between breastmilk levels of total fucosylated HMOs and number of night awakenings quantified by the BISQ. There was a correlation between the two variables for infant of 3 months of age.

DETAILED DESCRIPTION OF THE INVENTION

As used herein, the following terms have the following meanings.

The term "Subject" refers to an infant, young child, small for gestational age (SGA) or a preterm.

The term "infant" means a child under the age of 12 months.

The expression "young child" means a child aged between one and three years, also called toddler.

A "preterm" or "premature" means an infant or young child who was not born at term. Generally it refers to an infant or young child born prior 36 weeks of gestation.

By the expression "small for gestational age" or "SGA" it is referred to an infant or young child who is smaller in size than normal for their gestational age at birth, most commonly defined as a weight below the 10th percentile for the gestational age. In some embodiments, SGA may be associated with Intrauterine growth restriction (IUGR), which refers to a condition in which a foetus is unable to achieve its potential size.

The expression "nutritional composition" means a composition which nourishes a subject. This nutritional composition is usually to be taken orally or intravenously. It may include a lipid or fat source, a carbohydrate source and/or a protein source. In a particular embodiment the nutritional composition is a ready-to-drink composition such as a ready-to-drink formula.

The expression "sleep maturation or maturation of sleeping patterns" refers to the amelioration of the sleep quality and/or quantity in the framework of a longitudinal perspective of development for the subject. In one embodiment, the term also refers to the development of night and day sleep pattern from a more fragmented sleep composed of frequent short bout of sleeps and absence of circadian cycle immediately after birth, to a more adult-like sleep pattern, with long uninterrupted night sleep, limited day sleep and presence of circadian cycle.

Within the context of the present invention, the term "sleep quality" is characterized, comprised or is limited to sleep satisfaction as rated by caretaker, sleep problems as rated by caretaker and/or number of night awakenings. For the sake of clarity, higher sleep satisfaction and reduced sleep problems and/or night awakenings contribute to an improvement in sleep quality.

Within the context of the present invention, the term "sleep efficiency" indicates the ratio of total sleep time to time in bed.

Within the context of the present invention, the term "sleep quantity" is characterized, comprised or is limited to the length of night sleep, length of day sleep, time of total sleep duration (night & time sleep), in association to the number of episodes of wake states. For the sake of clarity, longer night sleeps and reduced number of episodes of night awakenings contribute to an improvement in sleep quantity and are an important marker of sleep maturation.

The "BISQ" questionnaire is the brief infant sleep questionnaire, this questionnaire has been developed to screen sleep problems in infants and young children. This questionnaire has also been commonly used in sleep research to quantify quantity and quality of sleep as well as sleep maturation (Sadeh A. "Sleep assessment method" Monographs Soc Res Child Dev 80(1) 2015).

In the framework of the BISQ questionnaire one or more parameters are observed and recorded that are selected in the group consisting of: nocturnal sleep duration (between the hours of 7 pm and 7 am); daytime sleep duration (between the hours of 7 am and 7 pm); number of night awaking; duration of wakefulness during the night hours (10 pm to 6 am); nocturnal sleep-onset time (the clock time at which the child falls asleep for the night); settling time (latency to falling asleep for the night); method of falling asleep; location of sleep; and preferred body position.

In a particular embodiment the nutritional composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic nutritional composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards and includes growing-up milk. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The term "fortifier" refers to liquid or solid nutritional compositions suitable for mixing with breast milk or infant formula.

The "mother's milk" should be understood as the breast milk or the colostrum of the mother.

The term "HMO" or "HMOs" refers to human milk oligosaccharide(s). These carbohydrates are resistant to enzymatic hydrolysis by digestive enzymes (e.g pancreatic and/or brush border), indicating that they may display functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide). Some examples of HMOs are the fucosylated oligosaccharides, the N-acetylated oligosaccharides and/or the sialylated oligosaccha rides.

A "fucosylated oligosaccharide" is an oligosaccharide having a fucose residue. It has a neutral nature. Some examples are 2-FL (2'-fucosyllactose), 3-FL (3-fucosyllactose), lactodifucosyllactose (LDFT), Lacto-N-difucohexaose (LNDFH), Lacto-N-neofucopentaose (LNnFP), difucosyllacto-N-hexaose a (DFLNHa), A-tetrasaccharides, lactodifucosyllactose (LDFT), lacto-N-difucosylhexose (LNDFH), Lacto-N-neodifucohexaose (LNnDFH), monofucosyllacto-N-hexaose, (I) MFLNH III, Fucosyl LST (a and b), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof.

A "sialylated oligosaccharide" is a charged sialic acid containing oligosaccharide, i.e. an oligosaccharide having a sialic acid residue. It has an acidic nature. In the present invention the sialylated oligosaccharide is 3-SL (3' sialyllactose). The expressions "sialylated oligosaccharide" and "sialyllactose (SL)" can be used interchangeably. The trisaccharide sialyllactose consists of lactose at the reducing terminus and one sialic acid residue at the non-reducing end via α-2,3 binding, resulting in 3'-sialyllactose (3'-SL), respectively.

A "precursor of HMO" is a key compound that intervenes in the manufacture of HMO, such as sialic acid and/or fucose.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

The nutritional composition according to the invention can be for example an infant formula, a starter infant formula, a follow-on or follow-up formula, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

The nutritional composition according to the invention generally contains a protein source. The protein can be in an amount of from 1.5 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s). In some particular embodiments of the invention, the nutritional composition of the invention does not comprise any carotenoid.

If the final product is to be a powder, the homogenised mixture is transferred to a suitable drying apparatus such as a spray dryer or freeze dryer and converted to powder. The powder should have a moisture content of less than about 5% by weight. The sialylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement. The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm. Preterm infants may be at increased risk of poor nutrient utilization, impaired lean body mass growth, fat accumulation in the visceral area and metabolic disease later in life. So in a particular embodiment the nutritional composition of the invention is for use in preterm infants.

The nutritional composition of the present invention may also be used in an infant or a young child that was born by C-section or that was vaginally delivered.

In some embodiments the nutritional composition according to the invention can be for use before and/or during the weaning period.

In some embodiments the nutritional composition according to the invention is for use in a subject at risk and/or in need.

The subject at risk and/or in need may be bottle-fed and/or formula-fed. The infants or young children at risk and/or in need may be infants or young children who have difficulties associated to sleep maturation.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on formula.

The different embodiments, details and examples previously described in the specification (e.g. related to the types and amounts of oligosaccharide, the nutritional composition, the administration, the targeted population . . . ) also apply to all these other objects.

EXAMPLES

The following examples illustrate some specific embodiments of the composition for use according to the present invention. The examples are given solely for the purpose of illustration and are not to be construed as limitations of the present invention, as many variations thereof are possible without departing from the spirit of the invention.

Example 1

In this example, we leverage the LIFE Child Cohort published in BMC Public Health 2012, 12:1021, aiming to monitor infant growth, development and health, where typically developing children from 0-6 years of age were enrolled, a detailed health assessment was conducted, and brief infant sleep questionnaire (BISQ) were administered at each visit. The LIFE child cohort collected breast milk from mothers of the included in the breast-fed infants at the time of the visit. We aimed to determine if associations exist between HMOs and sleep using BISQ.

A subset of typically developing children enrolled in the LIFE Child cohort aged between 0-12 months who were breast-fed at the time of visit were included in this study. and consists of breast milk samples—collected in mothers at 3, 6 and 12 months after child's birth—and questionnaires—collected during pregnancy and the first year of the child's life—containing information about children sleep (BISQ-Brief Infant Sleep Questionnaire) and some related confounding factors. the analysis was conducted on 153 subjects at 3 months, 113 subjects at 6 months and 27 subjects at 12 months. The collected BMs were analyzed for HMOs, including 2'-Fucosyllactose (2FL), 3'-Fucosyllactose (3FL), 3'-lactose (3SL), 6'-Sialyllactose (6SL), Lacto-N-tetraose (LNT), Lacto-N-neotetraose (LNnT), Lacto-N-fucopentaose I (LNFP1), and A-Tetrasaccharide. The association between sleep parameters generated using the BISQ and breast milk HMO levels were evaluated using logistic regression models adjusted for confounders (Gestational age, child gender, Number of months of exclusive breast feeding, smoke exposure, mother age at delivery, number of sibblings, socioeconomic status, method of falling asleep, sleeping location, dual parental household, kindergarten attendance, allergy, presence of rash). Number of night awakenings at were negatively correlated with sum of fucosylated HMOs at 6 months of age (p=0.05, FIG. 1). A decrease of number of awakening represents a maturation of sleep pattern.

The invention claimed is:

1. A method for improving sleep maturation in an infant or a young child in need thereof, the method comprising administering to the infant or young child a nutritional composition comprising fucosylated human milk oligosaccharides, wherein the nutritional composition does not comprise probiotics.

2. The method according to claim 1, wherein the fucosylated human milk oligosaccharides are selected from the group consisting of 2-FL (2' fucosyllactose), 3-FL (3-fucosyllactose), lactodifucosyllactose (LDFT), Lacto-N-difucohexaose (LNDFH), Lacto-N-neofucopentaose (LNnFP), difucosyllacto-N-hexaose a (DFLNHa), A-tetrasaccharides, lactodifucosyllactose (LDFT), lacto-N-difucosylhexose (LNDFH), Lacto-N-neodifucohexaose (LNnDFH), monofucosyllacto-N-hexaose, (I) MFLNH III, Fucosyl LST (a and b), difucosyllactose, lacto-N-fucopentaose, lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof.

3. The method according to claim 1, wherein the fucosylated human milk oligosaccharides are present in a total amount of from 50 mg to 5000 mg/L of the nutritional composition.

4. The method according to claim 1, wherein the sleep maturation is assessed on the basis of a questionnaire to quantify quantity and quality of sleep (BISQ).

5. The method according to claim 1, wherein sleep maturation is associated to a reduced number of episodes of night awakenings.

6. The method according to claim 1, wherein the nutritional composition is in a form selected from the group consisting of an infant formula, a starter infant formula, a follow-on or follow-up infant formula, a baby food, an infant cereal composition, a fortifier or a supplement.

7. The method according to claim 2, wherein the lacto-N-fucopentaose is selected from the group consisting of lacto-N-fucopentaose I, lacto-N-fucopentaose II, lacto-N-fucopentaose III, lacto-N-fucopentaose V and any combination thereof.

8. The method according to claim 1, wherein the infant or the young child is small for gestational age (SGA) or a preterm infant or young child.

9. The method according to claim 1, wherein the nutritional composition is an infant formula.

10. The method according to claim 1, wherein the nutritional composition comprises a carbohydrate source.

11. The method according to claim 10, wherein the carbohydrate source is lactose.

12. The method according to claim 1, wherein the nutritional composition comprises a protein source and wherein at least 90% of proteins of the protein source are intact.

* * * * *